US011500975B2

(12) United States Patent
Chen et al.

(10) Patent No.: US 11,500,975 B2
(45) Date of Patent: Nov. 15, 2022

(54) AUTHENTICATION DEVICE, AUTHENTICATION METHOD, AND COMPUTER PROGRAM

(71) Applicants: The Public University Corporation, The University of Aizu, Fukushima (JP); SIMPLEX QUANTUM Inc., Tokyo (JP)

(72) Inventors: Wenxi Chen, Fukushima (JP); Ying Chen, Fukushima (JP); Yuji Hamada, Tokyo (JP)

(73) Assignees: THE PUBLIC UNIVERSITY CORPORATION, THE UNIVERSITY OF AIZU, Fukushima (JP); SIMPLEX QUANTUM INC., Tokyo (JP)

( * ) Notice: Subject to any disclaimer, the term of this patent is extended or adjusted under 35 U.S.C. 154(b) by 538 days.

(21) Appl. No.: 16/725,916

(22) Filed: Dec. 23, 2019

(65) Prior Publication Data
US 2020/0134152 A1 Apr. 30, 2020

Related U.S. Application Data

(63) Continuation of application No. PCT/JP2018/024397, filed on Jun. 27, 2018.

(30) Foreign Application Priority Data

Jun. 27, 2017 (JP) .............................. JP2017-124730

(51) Int. Cl.
*G06K 9/00* (2022.01)
*G06F 21/32* (2013.01)
(Continued)

(52) U.S. Cl.
CPC ........... *G06F 21/32* (2013.01); *G06K 9/6215* (2013.01); *G06N 3/0454* (2013.01); *G06N 3/08* (2013.01)

(58) Field of Classification Search
USPC ....................................................... 713/186
See application file for complete search history.

(56) References Cited

U.S. PATENT DOCUMENTS 10,548,515 B2 * 2/2020 Pan ........................ A61B 5/117
2006/0136744 A1 * 6/2006 Lange ................ G06K 9/00536
713/186

(Continued)

FOREIGN PATENT DOCUMENTS

JP 2002-175515 A 6/2002
JP 2008-518709 A 6/2008

(Continued)

OTHER PUBLICATIONS

International Search Report issued by the International Search Authority corresponding to International Application No. PCT/JP2018/024397, dated Aug. 28, 2018.

*Primary Examiner* — Van D Huynh
(74) *Attorney, Agent, or Firm* — ArentFox Schiff LLP

(57) ABSTRACT

An authentication method comprising creating electrocardiogram data of users; calculating a similarity between electrocardiogram data of each user and template data created by averaging electrocardiogram data of each user; creating and training a first NNmodel for every user by using similarities between electrocardiogram data of a user and template data of the same user and similarities between electrocardiogram data of a user and template data of another user, and creating and training second NNmodels for users by using similarities between electrocardiogram data of a user and template data of the user and similarities between electrocardiogram data of the user and template (Continued)

data of another user; and executing a first step in which the similarities calculated using electrocardiogram data for authentication of a user to be authenticated and template data are input to the first NNmodel, and executing a second step in which the similarities are input to the second NNmodels.

8 Claims, 14 Drawing Sheets

(51) Int. Cl.
*G06K 9/62* (2022.01)
*G06N 3/04* (2006.01)
*G06N 3/08* (2006.01)

(56) References Cited

U.S. PATENT DOCUMENTS

| | | | | |
|---|---|---|---|---|
| 2007/0265540 | A1* | 11/2007 | Fuwamoto | A61B 5/35 600/515 |
| 2010/0049069 | A1* | 2/2010 | Tarassenko | A61B 5/7267 600/512 |
| 2010/0056939 | A1* | 3/2010 | Tarassenko | A61B 5/7267 600/509 |
| 2014/0225977 | A1* | 8/2014 | Vilcovsky | G06Q 50/00 348/14.07 |
| 2016/0063231 | A1* | 3/2016 | Bae | H04L 63/0861 340/5.82 |
| 2016/0063233 | A1* | 3/2016 | Bae | G07C 9/37 726/19 |
| 2016/0191517 | A1* | 6/2016 | Bae | H04L 63/0861 726/7 |
| 2016/0270699 | A1* | 9/2016 | Fernando | A61B 5/352 |
| 2016/0378965 | A1* | 12/2016 | Choe | A61B 5/352 726/19 |
| 2017/0188971 | A1* | 7/2017 | Liu | A61B 5/7267 |
| 2017/0215806 | A1* | 8/2017 | Bae | G06F 21/32 |
| 2017/0242974 | A1* | 8/2017 | Zhao | A61B 5/0245 |

FOREIGN PATENT DOCUMENTS

| | | |
|---|---|---|
| JP | 2010-510850 A | 4/2010 |
| JP | 2010-510851 A | 4/2010 |
| JP | 2012-038913 A | 2/2012 |
| JP | 2012-176106 A | 9/2012 |
| JP | 2014-239737 A | 12/2014 |
| JP | 2016-045939 A | 4/2016 |
| JP | 2016-049449 A | 4/2016 |
| JP | 2016-126775 A | 7/2016 |
| JP | 2016-171983 A | 9/2016 |
| JP | 2016-532197 A | 10/2016 |

* cited by examiner

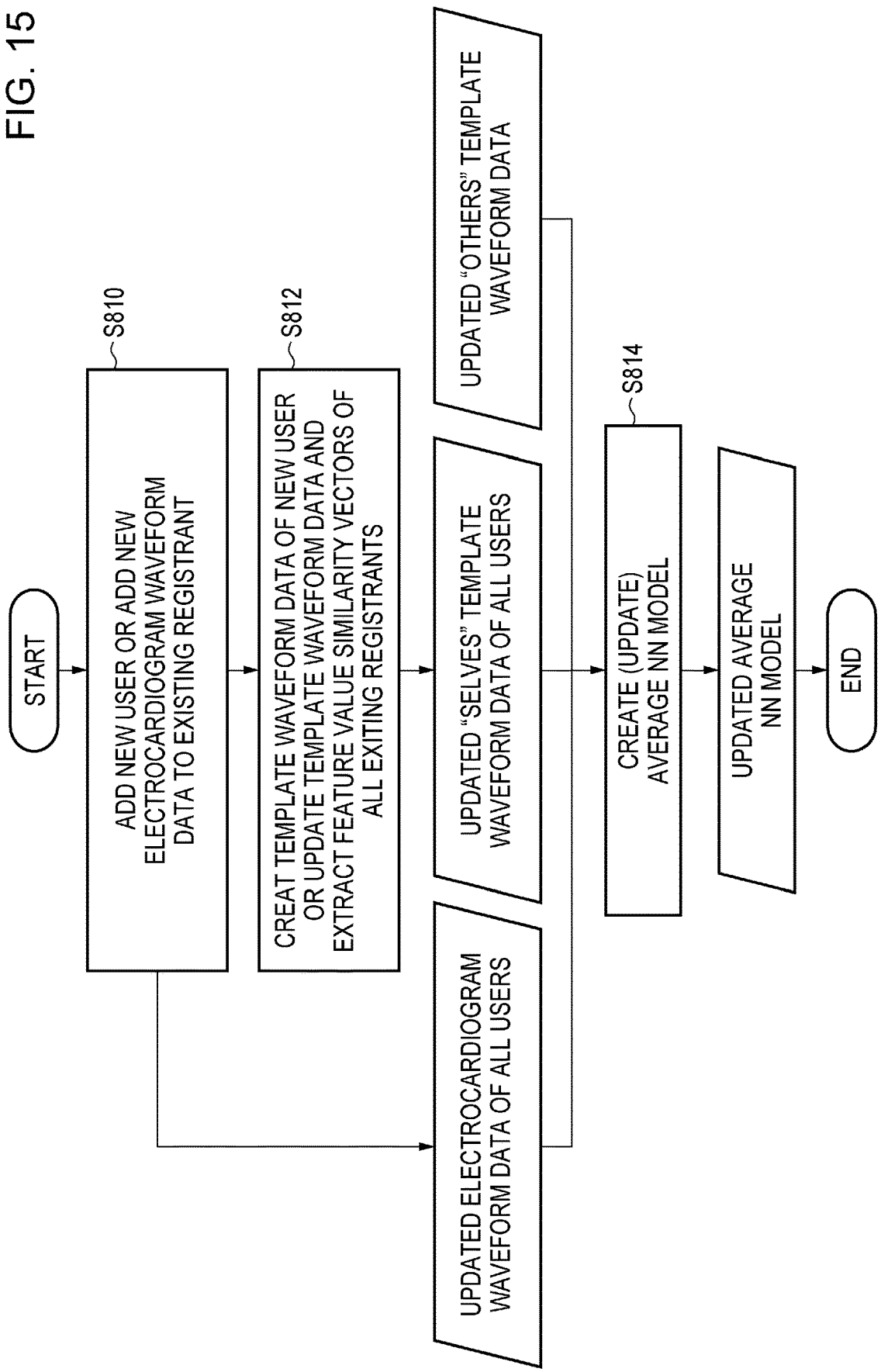

ature value is within the corresponding feature value range. However, if the feature value range is extended (i.e., the threshold value is reduced), then the false rejection rate is kept low, but the risk of falsely accepting another person may also increase. Also, it is difficult to update the feature value range according to a change with time.

AUTHENTICATION DEVICE, AUTHENTICATION METHOD, AND COMPUTER PROGRAM

CROSS-REFERENCE TO RELATED APPLICATION

This application is a continuation application of International Application No. PCT/JP2018/024397, filed on Jun. 27, 2018 and designated the U.S., the entire contents of which are incorporated herein by reference. Further, this application is based upon and claims the benefit of priority from the prior Japanese Patent Application No. 2017-124730, filed on Jun. 27, 2017, the entire contents of which are incorporated herein by reference.

FIELD

The present invention relates to an authentication device and an authentication method for authenticating a person using an electrocardiogram waveform of the person, and a computer program for causing a computer device to execute the authentication method.

BACKGROUND

As authentication means using biometric information of a person, there have been proposed various authentication methods for authenticating a person in a manner that electrocardiogram signals of the person are measured and an electrocardiogram waveform for each heartbeat extracted from the electrocardiogram signals is used. For example, see Japanese Patent Application Publication No. 2012-176106, Japanese Patent Application Publication No. 2016-171983, Japanese Patent Application Publication No. 2014-239737, Japanese Patent Application Publication No. 2016-126775, Japanese Patent Application Publication No. 2016-049449, Japanese Patent Application Publication No. 2016-045939, and Japanese Patent Application Publication No. 2012-038913.

As is known, characteristic waves such as a P wave, a Q wave, an R wave, an S wave, and a T wave appear in an electrocardiogram waveform of each heartbeat. Personal authentication is performed in a manner that feature information (amplitude, time width, interval between waves, slope, etc.) is extracted, the feature information to be authenticated is compared with feature information of each person registered in advance, and its correlation is determined.

SUMMARY

The electrocardiogram waveform varies from heartbeat to heartbeat even in the same person, and his/her physical condition, posture, and exercise state (including whether resting or exercising) also cause the variations. In addition, the electrocardiogram waveform varies with time. In order to extract a P wave, a Q wave, a R wave, a S wave, and a T wave in an electrocardiogram waveform with a high degree of accuracy to identify a person, it may be necessary to analyze the variations of a plurality of electrocardiogram waveforms and perform complex processing.

For example, Japanese Patent Application Publication No. 2014-239737 discloses that several types of feature values are extracted from electrocardiogram signals, a range (feature value range) within which each feature value is likely to fall in consideration of variations is determined, and the person is identified as the authorized person if the feature value is within the corresponding feature value range. However, if the feature value range is extended (i.e., the threshold value is reduced), then the false rejection rate is kept low, but the risk of falsely accepting another person may also increase. Also, it is difficult to update the feature value range according to a change with time.

Therefore, an object of the present invention is to provide an authentication device, an authentication method, and a computer program for causing a computer device to execute the authentication method, capable of performing a personal authentication with high accuracy by reducing both the false rejection rate and the false acceptance rate by a novel approach.

In order to achieve the above object, an authentication device according to the present invention includes an electrocardiographic waveform data creation unit configured to create a plurality of pieces of electrocardiogram waveform data extracted for each heartbeat from electrocardiogram signals of a plurality of users; a similarity calculation unit configured to calculate a similarity between each piece of electrocardiogram waveform data of each user and template waveform data created by averaging pieces of electrocardiogram waveform data of the each user; a neural network model creation unit configured to create and train a first neural network model for every user by using similarities between pieces of electrocardiogram waveform data of a user and the template waveform data of the same user and similarities between pieces of electrocardiogram waveform data of one user and the template waveform data of another user, and create and train a plurality of second neural network models for respective users by using similarities between pieces of electrocardiogram waveform data of a certain user and the template waveform data of the certain user and similarities between pieces of electrocardiogram waveform data of the certain user and the template waveform data of another user different from the certain user; and an authentication unit configured to, at the time of authentication, execute a first step of authentication process in which the similarities calculated using electrocardiogram waveform data for authentication created from electrocardiogram signals of a user to be authenticated and the template waveform data are input to the first neural network model created and trained in advance, and execute a second step of authentication process in which the similarities are input to the second neural network model created and trained in advance.

Further, an authentication method according to the present invention includes creating a plurality of pieces of electrocardiogram waveform data extracted for each heartbeat from electrocardiogram signals of a plurality of users; calculating a similarity between each piece of electrocardiogram waveform data of each user and template waveform data created by averaging pieces of electrocardiogram waveform data of the each user; creating and training a first neural network model for every user by using similarities between pieces of electrocardiogram waveform data of a user and the template waveform data of the same user and similarities between pieces of electrocardiogram waveform data of one user and the template waveform data of another user, and creating and training a plurality of second neural network models for respective users by using similarities between pieces of electrocardiogram waveform data of a certain user and the template waveform data of the certain user and similarities between pieces of electrocardiogram waveform data of the certain user and the template waveform data of another user different from the certain user; and at the time of authentication, executing a first step of authentication process in which the similarities calculated using electrocardiogram waveform data for authentication created from electrocardiogram signals of a user to be authenticated and the template waveform data are input to the first neural network model created and trained in advance, and executing a second step of authentication process in which the similarities are input to the second neural network model created and trained in advance.

According to the authentication device and the authentication method of the present invention, it is possible to perform a personal authentication with high accuracy in a short time. Updating the template waveform data and updating the neural network model in consideration of a change in the electrocardiogram signals with time make it possible to perform a long-term and continuous personal authentication.

BRIEF DESCRIPTION OF DRAWINGS

FIG. 15 is a flowchart of an average NN model update process.

DESCRIPTION OF EMBODIMENTS

Hereinafter, embodiments of the present invention will be described with reference to the drawings. However, such example embodiments do not limit the technical scope of the present invention.

Figure 1:
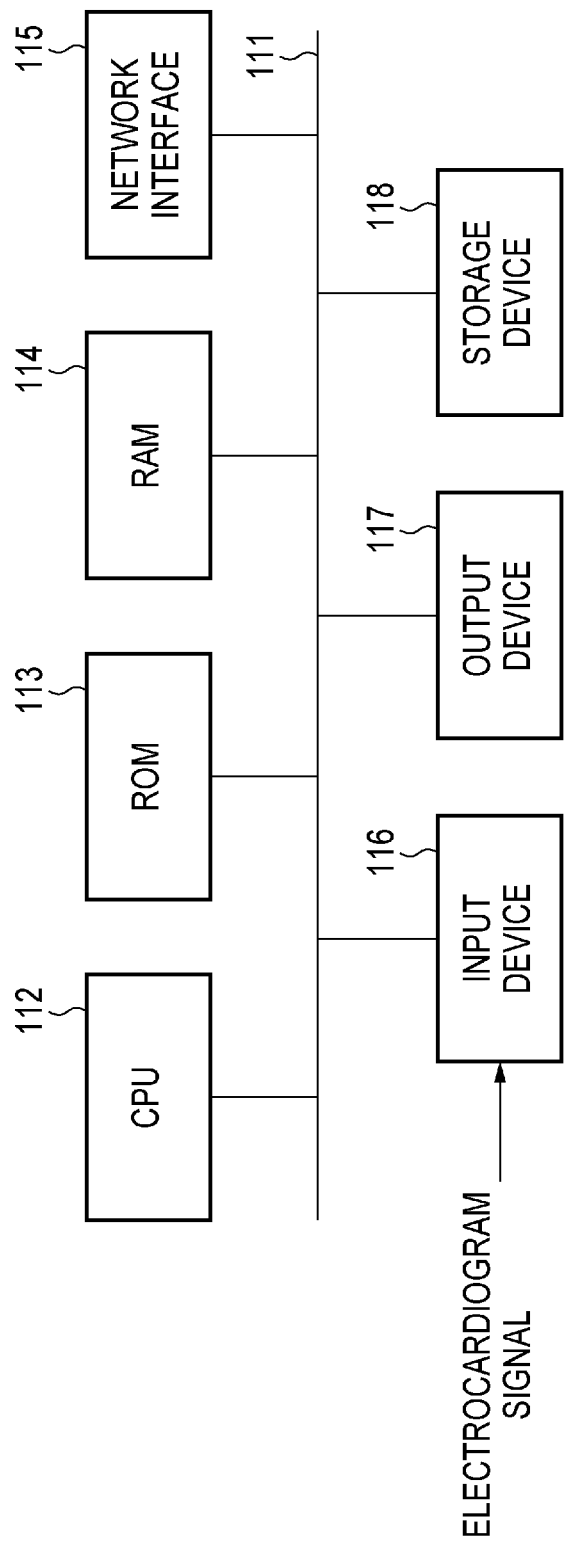
FIG. 1 illustrates a configuration example of an authentication device according to an embodiment of the present invention.

FIG. 1 illustrates a configuration example of an authentication device according to an embodiment of the present invention. The authentication device is a computer device, which may be a general-purpose personal computer, including any type such as desktop, laptop, and tablet. The personal authentication device has a hardware configuration of a general-purpose computer device. As an example, the authentication device includes a CPU 112, a ROM 113, a RAM 114, a network interface 115, an input device 116, an output device 117, and a storage device 118, which are connected to a bus 111.

The CPU 112 performs data processing or calculation and controls various components connected thereto via the bus 111, and functions as a setting unit, a calculation unit, and an output unit. The ROM 113 stores a control procedure (computer program) of the CPU 112 in advance, so that the computer device is activated when the CPU 112 executes the computer program. The storage device 118 is, for example, a storage medium such as a hard disk storage device or an optical disk medium (e.g., CD-ROM), and stores a computer program for executing the authentication processes according to the present embodiment and a database of, for example, waveform data of electrocardiogram signals, and the like. The computer program is read into the RAM 114 and executed by the CPU 112. The CPU 112 executes the computer program to execute various authentication processes according to the present embodiment described later. The RAM 114 is used as a work memory for input/output and transmission/reception of data, and temporary storage for control of each component.

The network interface 115 is an interface for connecting to the Internet. The input device 116 is connected by wire or wirelessly to a measurement device (not illustrated) for measuring an electrocardiogram signal, and receives the electrocardiogram signal measured by the measurement device. The output device 117 is a display unit, such as a display, including a printer serving as a display device for print out.

Figure 2:
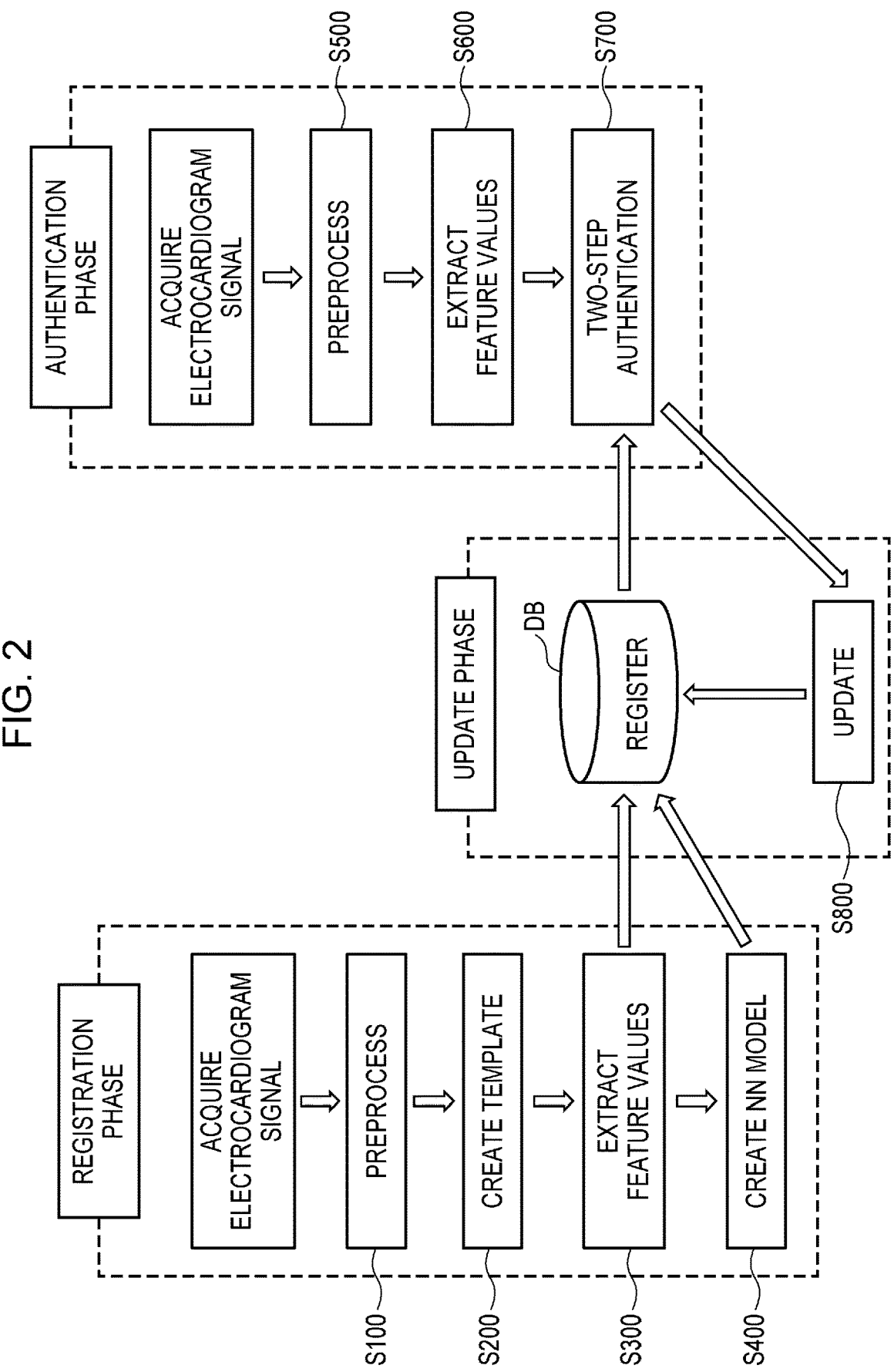
FIG. 2 is a functional block diagram illustrating functions of the authentication device according to the present embodiment.

FIG. 2 is a functional block diagram illustrating functions of the authentication device according to the present embodiment. The functions of the authentication device have processes of a registration phase, an authentication phase, and an update phase, and these functions are implemented by the CPU executing the computer program.

The registration phase has processes for registration: acquisition of an electrocardiogram signal of a person (hereinafter referred to as a user) at the time of registration; a preprocessing that performs preprocessing on the acquired electrocardiogram signal (S100); a template waveform data creation process that creates template waveform data for each user from the preprocessed waveform data (S200); a feature value extraction process that extracts feature values of the template waveform data and registers the feature values as a database (S300); and an NN model creation process that creates and trains two types of neural network (NN) models: "average model" and "personal model" which are described later by using the feature values and registers the NN models (S400).

The authentication phase has processes for authentication: acquisition of an electrocardiogram signal of a user at the time of registration; a preprocessing that performs preprocessing on the acquired electrocardiogram signal (S500); a feature value extraction process that extracts feature values of the preprocessed waveform data (S600); and a two-step authentication process that performs a first step of authentication process and a second step of authentication process in a manner that similarities between the feature values extracted at S600 and the feature values of the template waveform data registered at S300 are calculated and input into the two types of NN models (S700). When both of the authentication processes using the two types of NN models determine that the user is the authorized user (person himself/herself) in the two-step authentication process, the user is determined to be the authorized user.

The update phase has an update process that updates the template waveform data and the neural network models (NN models), which are created and registered in the registration phase, at any time or periodically by using the user electrocardiogram signals additionally acquired at the time of authentication (S800). Hereinafter, each function of the personal authentication device illustrated in FIG. 2 will be described.

Registration Phase

In the registration phase, a process for registering in advance information related to user electrocardiogram signals for authentication is executed.

Preprocess (S100)

Figure 3:
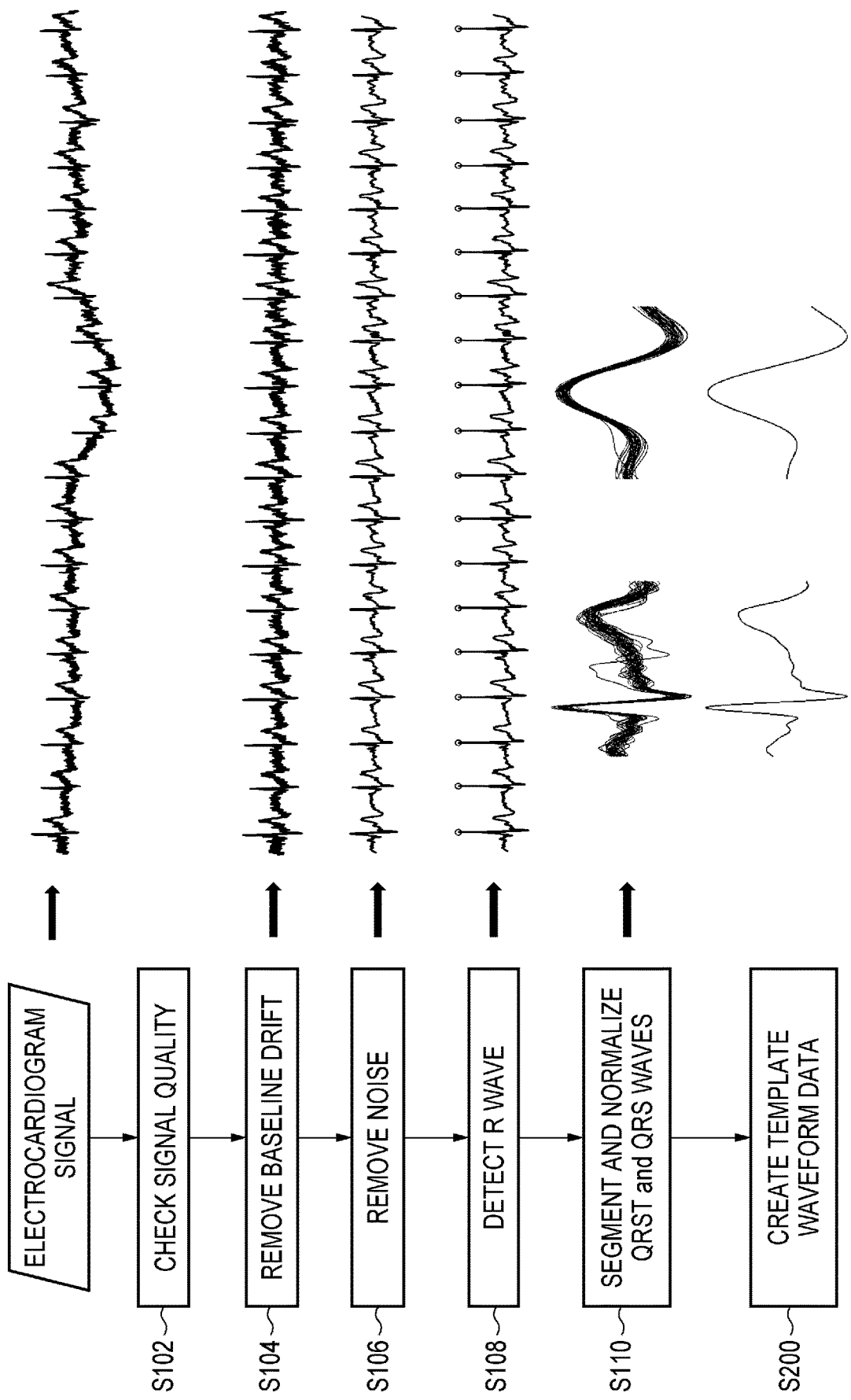
FIG. 3 is a flowchart of preprocessing of measured electrocardiogram signals.

FIG. 3 is a flowchart of preprocessing of measured electrocardiogram signals to be performed. When an electrocardiogram signal of the user to be registered is measured by the measurement device and the personal authentication device receives the measured electrocardiogram signal, a quality check process is performed on the signal (S102). The received electrocardiogram signal on which the quality check process is to be performed is of 30 seconds or 30 beats. The signal quality is determined depending on whether or not a kurtosis k of the electrocardiogram signal is within a threshold range, where the kurtosis k is defined and calculated by Equation (1). The kurtosis k is a scale indicating a degree of peakedness of the distribution. Further, $\mu$ is an average value of x, $\sigma$ is a standard deviation of x, and E(x) represents an expected value of x $$k = \frac{E(x-\mu)^4}{\sigma^4}$$  Equation (1)

Threshold value $\begin{cases} 3 < k \leq 30 & \text{Good quality} \\ k \leq 3 \text{ or } k > 30 & \text{Bad quality} \end{cases}$ (Reference range)

As a result of the quality check process, if the quality of the electrocardiogram signal does not satisfy a predetermined standard (i.e., if the kurtosis k is out of the threshold range), it waits for a predetermined time (e.g., 3 seconds), the authentication device then receives an electrocardiogram signal measured during another time, and the quality check process is performed on the electrocardiogram signal (S102). An electrocardiogram signal is repeatedly acquired until the acquired electrocardiogram signal indicates to have a kurtosis k within the threshold range.

When an electrocardiogram signal satisfying the quality standard of S102 is acquired, a baseline drift removal process (S104) is performed on the electrocardiogram signal. The baseline drift removal process is a process for suppressing the baseline drift of the electrocardiogram signal by wavelet decomposition.

Subsequently, a noise removal process (S106) may be performed using a notch filter and a low-pass filter, and a smoothing process may further be performed using a moving average filter.

An R peak is detected from each heartbeat waveform of the electrocardiogram signal subjected to various filtering (S108), and a QRST wave and a QRS wave are segmented for each heartbeat waveform based on the R peak to perform a normalization process (S110).

Figure 4:
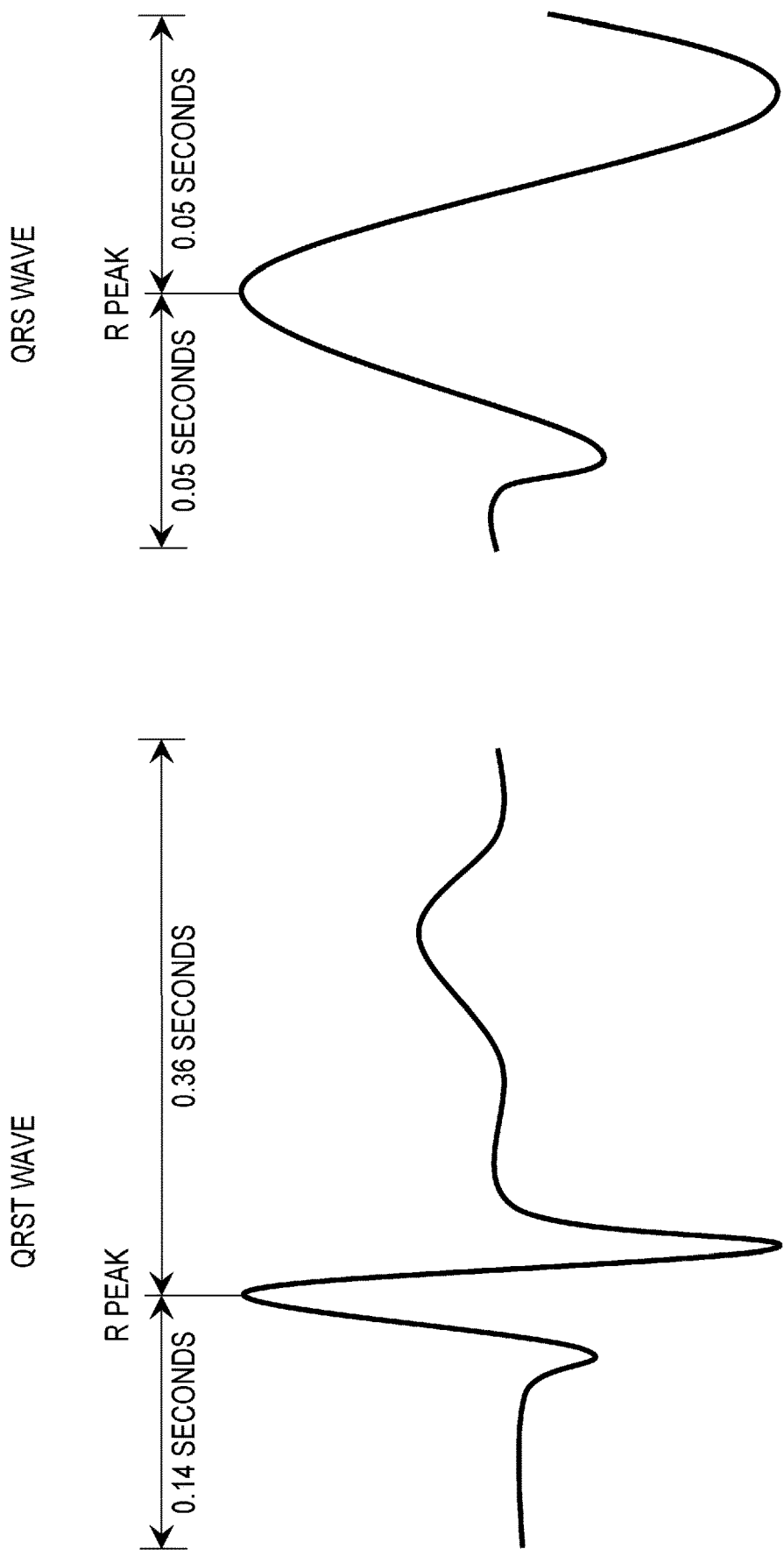
FIG. 4 is a diagram for explaining a QRST wave and QRS wave separation process.

FIG. 4 is a diagram for explaining a QRST wave and QRS wave separation process. Cutting out a waveform having a predetermined time width around the position of the R peak as a reference makes it possible to separate and extract a QRST wave and a QRS wave (hereinafter sometimes collectively referred to as "electrocardiogram waveform data") for each heartbeat. Each piece of electrocardiogram waveform data $x_i$, which is the segmented QRST wave or the segmented QRS wave, is normalized around the R peak by the following Equation (2), so that the normalized QRST wave and QRS wave are created. Here, $\mu_x$ is an average value of the segmented waveform data, and n is the length of x.

$$N = \frac{x_i - \mu_x}{n_x}$$  Equation (2)

A template QRST wave and a template QRS wave (hereinafter sometimes collectively referred to as "template waveform data") are created using the created QRST wave and QRS wave (electrocardiogram waveform data). Next, the template waveform data creation process (S200) will be described.

Template Waveform Data Creation Process (S200)

Figure 5:
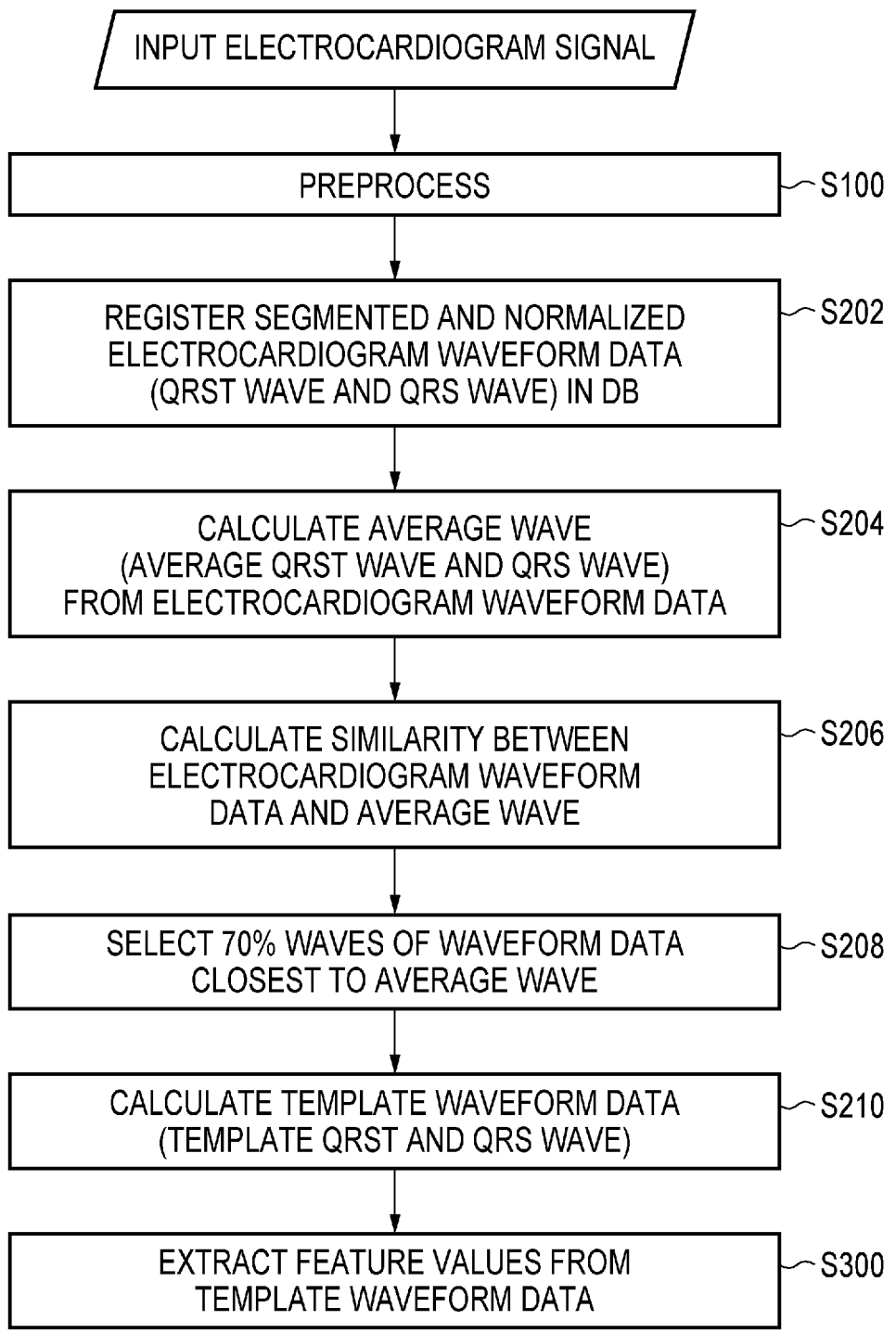
FIG. 5 is a flowchart of a template waveform data creation process.

FIG. 5 is a flowchart of the template waveform data creation process. The QRST wave and the QRS wave (electrocardiogram waveform data) for each heartbeat, which are created in the preprocessing (S100) described above, are stored in a database (DB) (S202). For example, if QRST waves and QRS waves of 30 beats are segmented from an electrocardiogram signal, the 30 QRST waves and the 30 QRS waves are registered in the database.

An average QRST wave that is an average wave of, for example, 30 QRST waves and an average QRS wave that is an average wave of, for example, 30 QRS waves are calculated (S204), and a similarity between each QRST wave and the average QRST wave and also a similarity between each QRS wave and the average QRS wave are calculated (S206). The similarity between each wave and the average wave (the average QRST wave and the average QRS wave are sometimes collectively referred to as the "average wave") can be determined based on, for example, a sum of Euclidean distances calculated between two waveforms to be compared. Then, based on the calculated similarity, QRST waves and QRS waves closest to the corresponding average wave, for example, 70% waves of the corresponding average wave are selected (S208). If, for example 30 QRST waves and, for example, 30 QRS waves are stored, 21 QRST waves and 21 QRS waves are selected in the order similar to the respective average waves (in descending order of similarity). The ratio (or number) of QRST waves and QRS waves to be selected is not limited to 70%, and a suitable value is set as appropriate.

Average waves of the QRST waves and the QRS waves selected at S208 are further calculated, and the average waves are set as a template QRST wave and a template QRS wave, respectively (S210). The template QRST wave and the template QRS wave are waveform data registered as personal heartbeat waveforms of a user whose electrocardiogram signals have been measured, and are waveform data used as a base of user authentication.

Feature values are extracted from the template QRST wave and the template QRS wave. Next, the feature value extraction process (S300) will be described.

Feature Value Extraction Process (S300)

Figure 6:
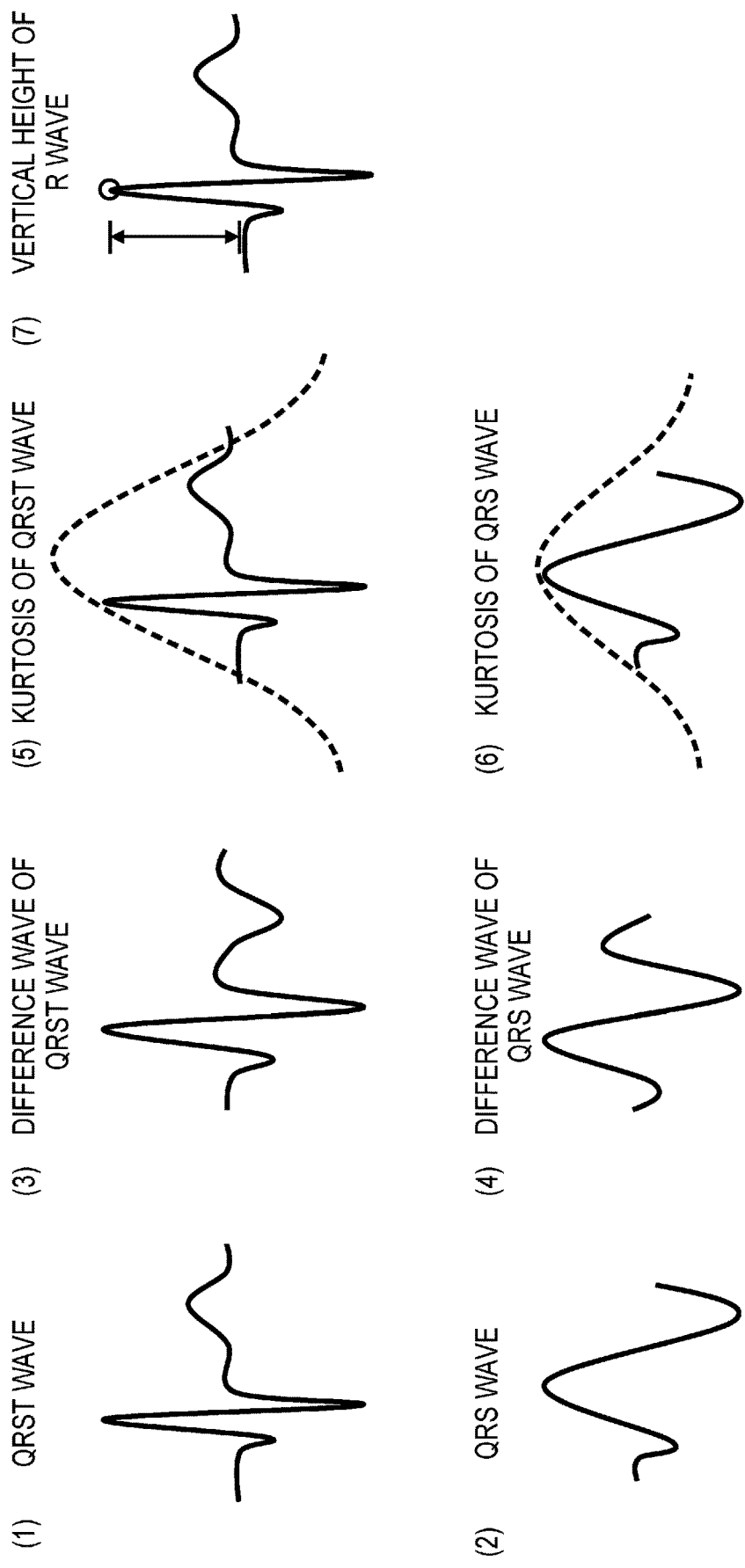
FIG. 6 is a diagram for explaining feature values extracted from a template QRST wave and a template QRS wave.

FIG. 6 is a diagram for explaining feature values extracted from the template QRST wave and the template QRS wave. The feature values are (1) time series data of the template QRST wave, (2) time series data of the template QRS wave, (3) time series data of a difference wave of the template QRST wave, and (4) time series data of a difference wave of the template QRS wave, (5) a kurtosis of the template QRST wave, (6) a kurtosis of the template QRS wave, and (7) a vertical height of the R peak. A combination of these seven types of feature values makes a feature value set. The types of feature values are not limited to these seven types, and other types of feature values may be used. In addition, the number of types of feature values is not limited to seven, may be more or less than seven. A suitable number of feature values and a suitable type of feature value may be selected.

Mainly extracting feature values from the QRST wave and the QRS wave makes it easy to extract the feature values without having detected a Q wave, an S wave, and a T wave, resulting in obtaining highly reliable values. Further, it is possible to extract the feature values from the waveform data for each heartbeat without having obtained a plurality of continuous heartbeats, and thus to reduce the influence of variations in heart rate, resulting in highly accurate extraction of feature values.

Figure 7:
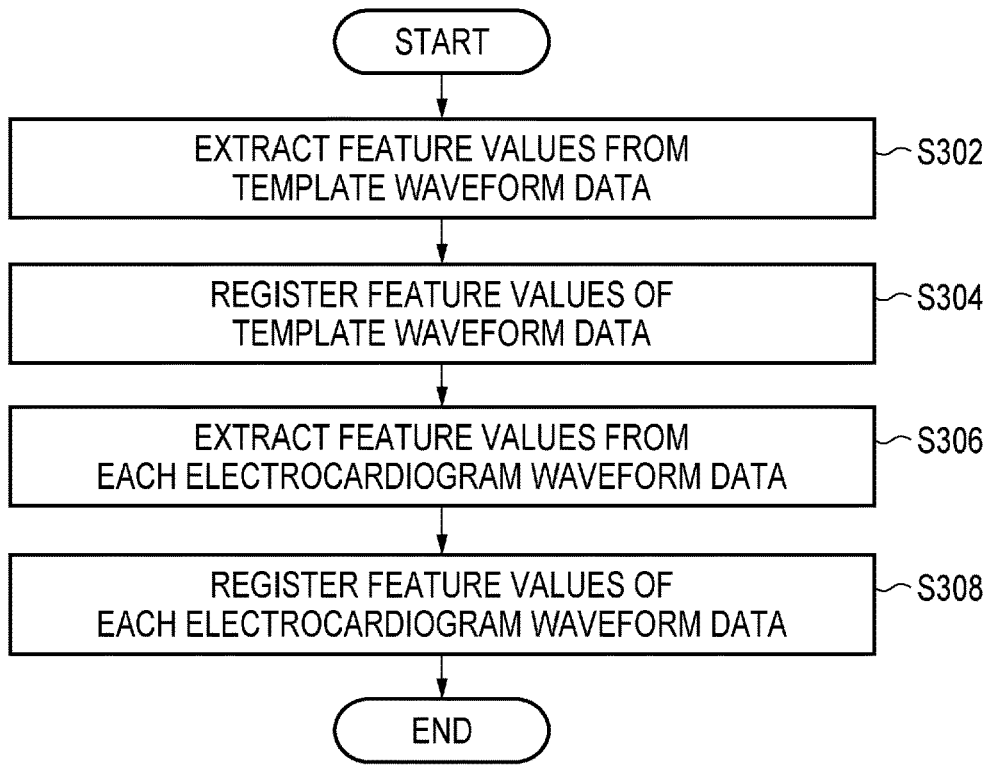
FIG. 7 is a flowchart of a feature value extraction process.

FIG. 7 is a flowchart of the feature value extraction process. The feature values described above are extracted from the template QRST wave and the template QRS wave (S302), and are stored and registered (S304). The feature values include (1) time series data of the template QRST wave and (2) time series data of the template QRS wave, and are registered in the database. Further, the feature values described above are also extracted from the respective pieces of electrocardiogram waveform data which are the QRST wave and the QRS wave obtained at S110 (S306), and are stored and registered (S308). As such, the feature values of the template waveform data are extracted and registered for each user, and further the feature values of each piece of electrocardiogram waveform data used for obtaining the template waveform data are extracted and registered for each user. Next, the neural network model creation process (S400) will be described.

Neural Network Model (NN Model) Creation Process

Figure 8:
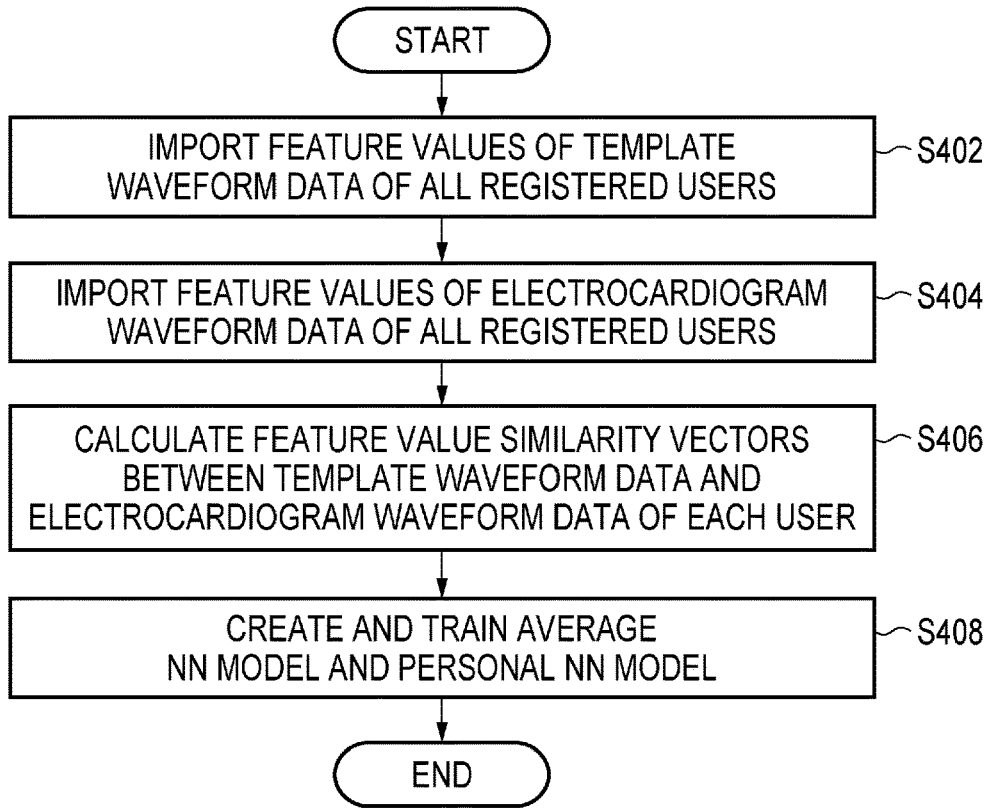
FIG. 8 illustrates a flowchart of a NN model creation process.

FIG. 8 illustrates a flowchart of the neural network model creation process. The feature values of the template waveform data of all the users registered at S304 of FIG. 7 are read (S402). Then, the feature values of the electrocardiogram waveform data (QRST wave and QRS wave) of all the users registered at S308 are read (S404).

A feature value similarity vector between the feature values of the template waveform data and the feature values of the electrocardiogram waveform data of each user is calculated (S406).

A similarity d between the feature value of the electrocardiogram waveform data and the feature value $\mu_x$ of the template waveform data is calculated by the following Equations (3-1) and (3-2). The feature values are the seven types described above: (1) time series data of the template QRST wave, (2) time series data of the template QRS wave, (3) time series data of a difference wave of the template QRST wave, and (4) time series data of a difference wave of the template QRS wave, (5) a kurtosis of the template QRST wave, (6) a kurtosis of the template QRS wave, and (7) a vertical height of the R peak. The similarities in these seven feature values are referred to as d1, d2, d3, d4, d5, d6, d7, respectively. The Euclidean distance is used to calculate the similarities d1, d2, d3, and d4, and the Manhattan distance is used to calculate the similarities d5, d6, and d7.

$$\left.\begin{array}{l}QRST \text{ wave } (d1) \\ QRS \text{ wave } (d2) \\ \text{Difference wave of } QRST \ (d3) \\ \text{Difference wave of } QRS \ (d4)\end{array}\right\} d(x_i, \mu_x) = \sqrt{\sum_{r=1}^{n}(y_r(x_i) - y_r(\mu_x))}$$ Equation (3-1)

$$\left.\begin{array}{l}\text{Kurtosis of } QRST \text{ wave } (d5) \\ \text{Kurtosis of } QRS \text{ wave } (d6) \\ \text{Vertical length of } R \text{ wave } (dl)\end{array}\right\} d(x_i, \mu_x) = |y_r(x_i) - y_i(\mu_x)|$$ Equation (3-2)

From the similarities d1, d2, d3, d4, d5, d6, and d7 calculated by Equations (3-1) and (3-2), the feature value similarity vector is expressed as Equation (4).

$$\text{Feature value similarity vector} = \begin{bmatrix} d1 \\ d2 \\ d3 \\ d4 \\ d5 \\ d6 \\ d7 \end{bmatrix}$$ Equation (4)

In the process of calculating the feature value similarity vector (S406), the feature value similarity vector (referred to as the feature value similarity vector for the "selves class") between the pieces of electrocardiogram waveform data of a user and the template waveform data of the same user is calculated for every user. In addition, the feature value similarity vector (referred to as the feature value similarity vector for the "others class") between the pieces of electrocardiogram waveform data of one user and the template waveform data of another user is also calculated. Two types of NN models: an average neural network model (NN model) and a personal NN model, are created and trained such that each model uses a different combination of the feature value similarity vector of the "selves class" and the feature value similarity vector of the "others class" (S408).

Figures 9A, 9B:
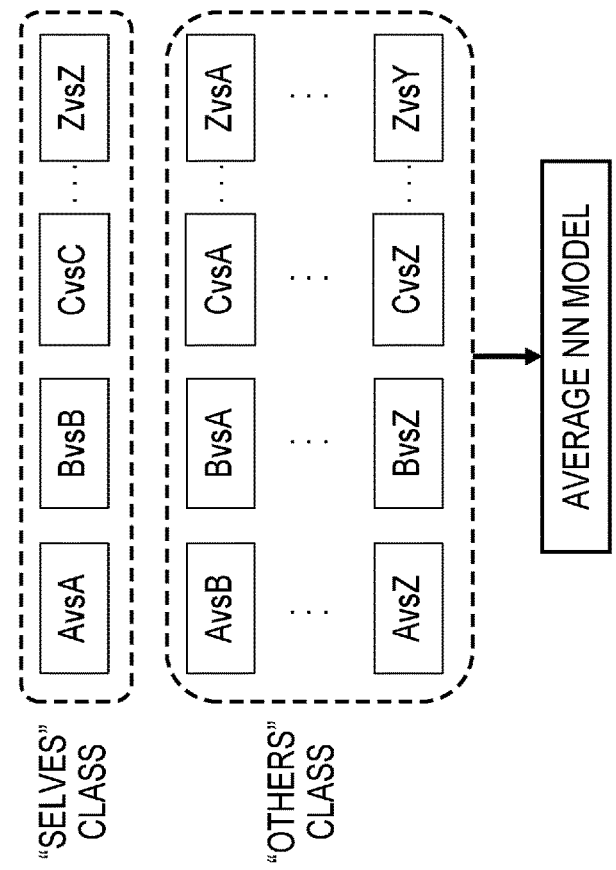
FIGS. 9A and 9B are diagrams for explaining a selves class and an others class of a feature value similarity vector.

FIGS. 9A and 9B are diagrams for explaining the selves class and the others class of the feature value similarity vector. FIG. 9A illustrates the feature value similarity vectors for the selves class and the others class used for the average NN model; and FIG. 9B illustrates the feature value similarity vectors for the selves class and the others class used for the personal NN model.

In a case where there are users A, B, . . . , Z (26 users), the feature value similarity vectors for the selves class include, for example, the feature value similarity vector (A vs. A) between the pieces of electrocardiogram waveform data of user A and the template waveform data of user A, the feature value similarity vector (B vs. B) between the pieces of electrocardiogram waveform data of user B and the template waveform data of user B, and the feature value similarity vector (Z vs. Z) between the pieces of electrocardiogram waveform data of user Z and the template waveform data of user Z. Each feature value similarity vector for the selves class indicates the feature value similarity vector between the pieces of electrocardiogram waveform data of a user and the template waveform data of the same user.

On the other hand, the feature value similarity vectors for the others class include, for example, the feature value similarity vector (A vs. B) between the pieces of electrocardiogram waveform data of user A and the template waveform data of user B, the feature value similarity vector (B vs. A) between the pieces of electrocardiogram waveform data of user B and the template waveform data of user A, the feature value similarity vector (Z vs. A) between the pieces of electrocardiogram waveform data of user Z and the template waveform data of user A, and the feature value similarity vector (Z vs. Y) between the pieces of electrocardiogram waveform data of user Z and the template waveform data of user Y. Each feature value similarity vector for the others class indicates the feature value similarity vector between the pieces of electrocardiogram waveform data of one user and the template waveform data of another user.

Only one average NN model is created. In a case where there are users A, B, . . . , Z, the average NN model is created using all the feature value similarity vectors for the selves class (A vs. A, . . . , Z vs. Z) and the feature value similarity vectors for the others class (feature value similarity vectors of different users excluding the feature value similarity vectors for the selves class).

The personal NN model is created for each user, resulting in personal NN models of the number of users. For example, the personal NN model of user A (model A) is created using the feature value similarity vector (A vs. A) for the selves class of user A and the feature value similarity vectors (A vs. B, . . . , A vs. Z) between the pieces of electrocardiogram waveform data of user A and the pieces of the template waveform data of the other users B to Z; the personal NN model of user B (model B) is created using the feature value similarity vector (B vs. B) for the selves class of user B and the feature value similarity vectors (B vs. A, B vs. C, . . . , B vs. Z) between the pieces of electrocardiogram waveform data of user A and the pieces of the template waveform data of the other users A, C to Z; and the personal NN model of user Z (model Z) is created using the feature value similarity vector (Z vs. Z) for the selves class of user Z and the feature value similarity vectors (Z vs. A, . . . , Z vs. Y) between the pieces of electrocardiogram waveform data of user Z and the pieces of the template waveform data of the other users A to Y.

Figure 10:
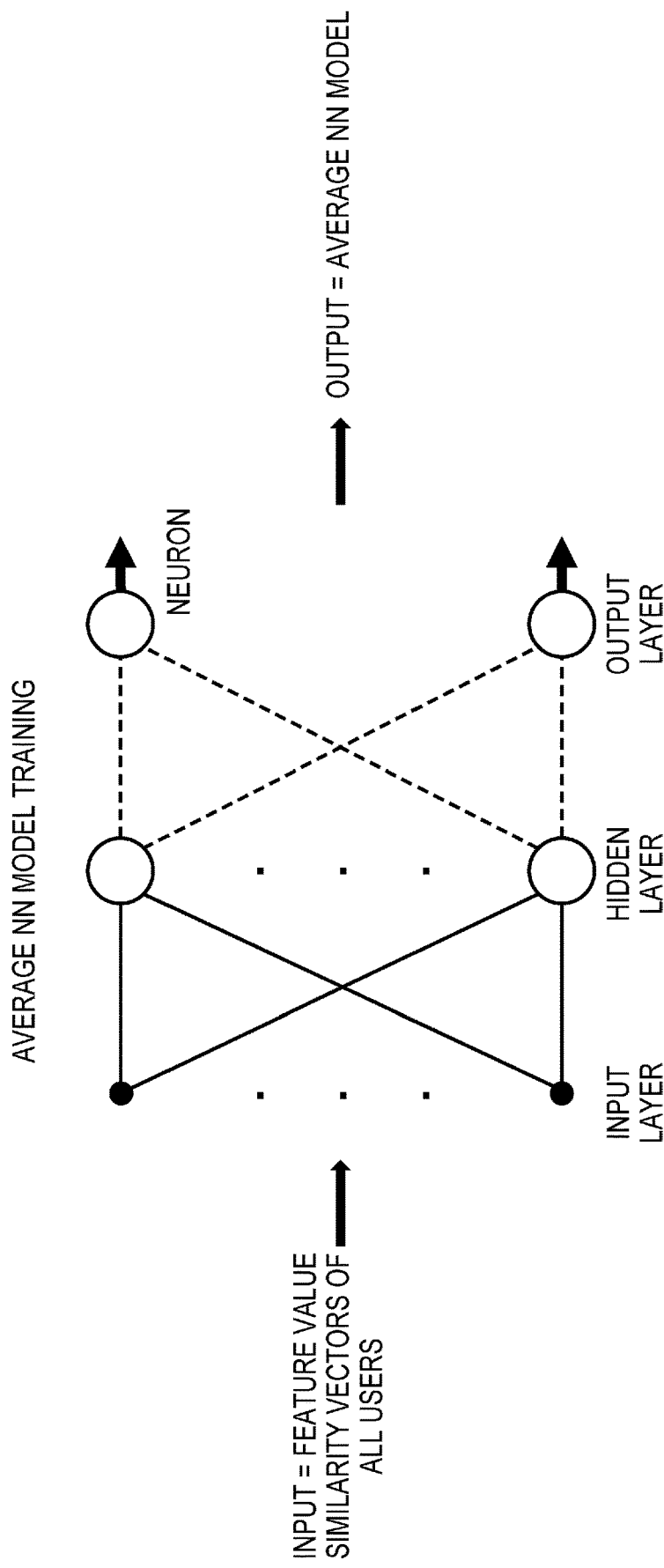
FIG. 10 is a diagram illustrating a creation and training process of an average NN model.

FIG. 10 is a diagram illustrating a process of creating and training the average NN model. As illustrated in FIG. 9A, the feature value similarity vectors to be input include the feature value similarity vectors for the selves class of all the users and the feature value similarity vectors for the others class of different users.

It is to be noted that the maximum number of feature value similarity vectors for the others class is enormous (25 times if the number of users is 26) as compared to the number of feature value similarity vectors for the selves class. In order to attain a balance between pieces of training data to be input to the NN model (proportional relationship between the numbers of feature value similarity vectors for the others class and the selves class), the number of feature value similarity vectors for the others class may be selected to be thinned out, for example, so as to be around two or three times the number of feature value similarity vectors for the selves class.

The average NN model is created and trained for the feature value similarity vectors to be input such that (1, 0) is output as a selves output in response to the input of a feature value similarity vector for the selves class, and (0, 1) is output as an others output in response to the input of a feature value similarity vector for the others class.

Figure 11:
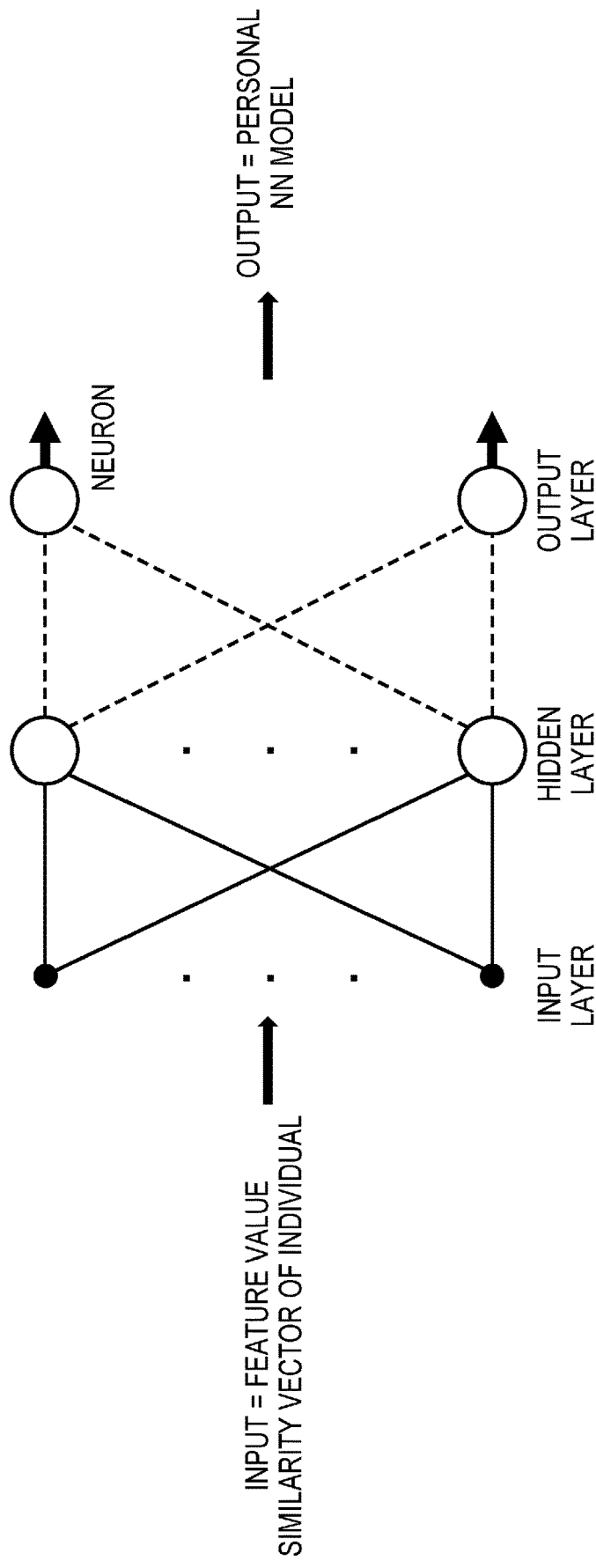
FIG. 11 is a diagram illustrating a creation and training process of a personal NN model.

FIG. 11 is a diagram illustrating a process of creating and training the personal NN model. As illustrated in FIG. 9B, the feature value similarity vectors to be input include the feature value similarity vectors for the selves class of respective users and the feature value similarity vectors for the others class of the other users.

It is to be noted that the number of feature value similarity vectors for the others class is enormous (25 times if the number of users is 26) as compared to the number of feature value similarity vectors for the selves class. Also for the personal NN model, in order to attain a balance between pieces of training data to be input to the NN model, the number of feature value similarity vectors for the others class may be selected to be thinned out, for example, so as to be around two or three times the number of feature value similarity vectors for the selves class.

For each user, the personal NN model is created and trained for the feature value similarity vectors to be input such that (1, 0) is output as a selves output in response to the input of a feature value similarity vector for the selves class, and (0, 1) is output as an others output in response to the input of a feature value similarity vector for the others class.

The created average NN model and personal NN model are registered in the database (S400). Next, processing in the authentication phase will be described.

Authentication Phase

The authentication phase is a process of measuring an electrocardiogram signal of a user to be authenticated and determining whether the measured electrocardiogram signal is of a user registered in the above-described registration phase (whether or not the user is the authorized user).

Preprocess (S500)

An electrocardiogram signal of a user to be authenticated is measured, and preprocessing of the measured signal is performed. This preprocessing is a process similar to the preprocessing (S100) in the registration phase illustrated in FIG. 2. Accordingly, the original segmented electrocardiogram waveform data (QRST wave and QRS wave) of the user to be authenticated is acquired.

Feature Value Extraction Process (S600)

The feature values illustrated in FIG. 6 are extracted for the electrocardiogram waveform data of the user to be authenticated by a process similar to the feature value extraction process (S300) in the registration phase.

Two-Step Authentication Process (S700)

Figure 12:
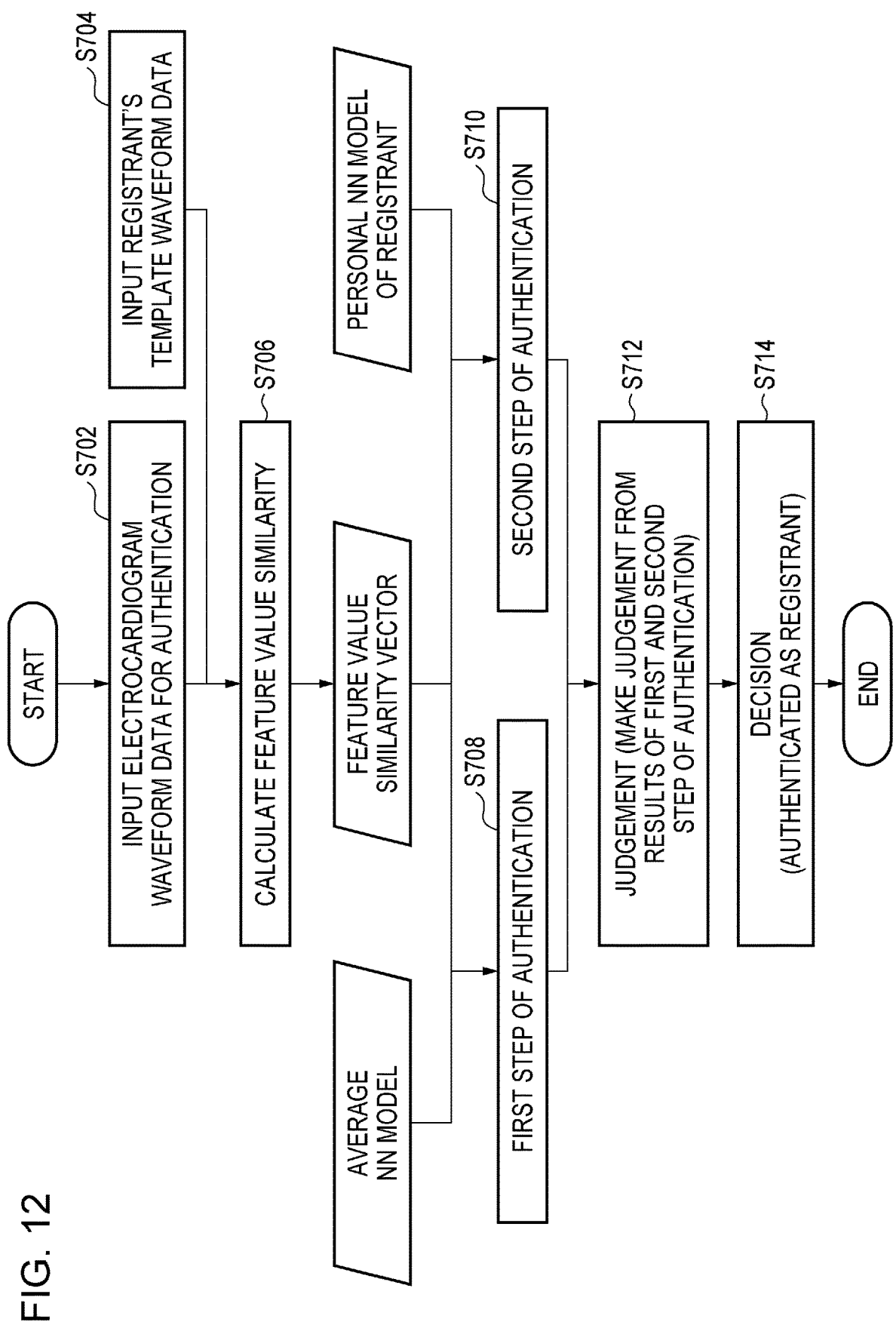
FIG. 12 is a flowchart of a two-step authentication process.

FIG. 12 is a flowchart of the two-step authentication process. A set of feature values of the electrocardiogram waveform data for each heartbeat of the user to be authenticated is sequentially selected and inputted (S702). A set of feature values of the template waveform data for each registered user is sequentially selected and inputted (S704). Then, their feature value similarity vectors are calculated (S706).

The calculated feature value similarity vectors are input to both the average NN model and the personal NN model which are created in the registration phase (or updated in the update phase described later), so that the first step of authentication process (S708) based on the average NN model and the second step of authentication process (S710) based on the personal NN model are performed. For one piece of electrocardiogram waveform data, one authentication using one average NN model and authentication using all the personal NN models for the number of registered users are performed.

Figure 13:
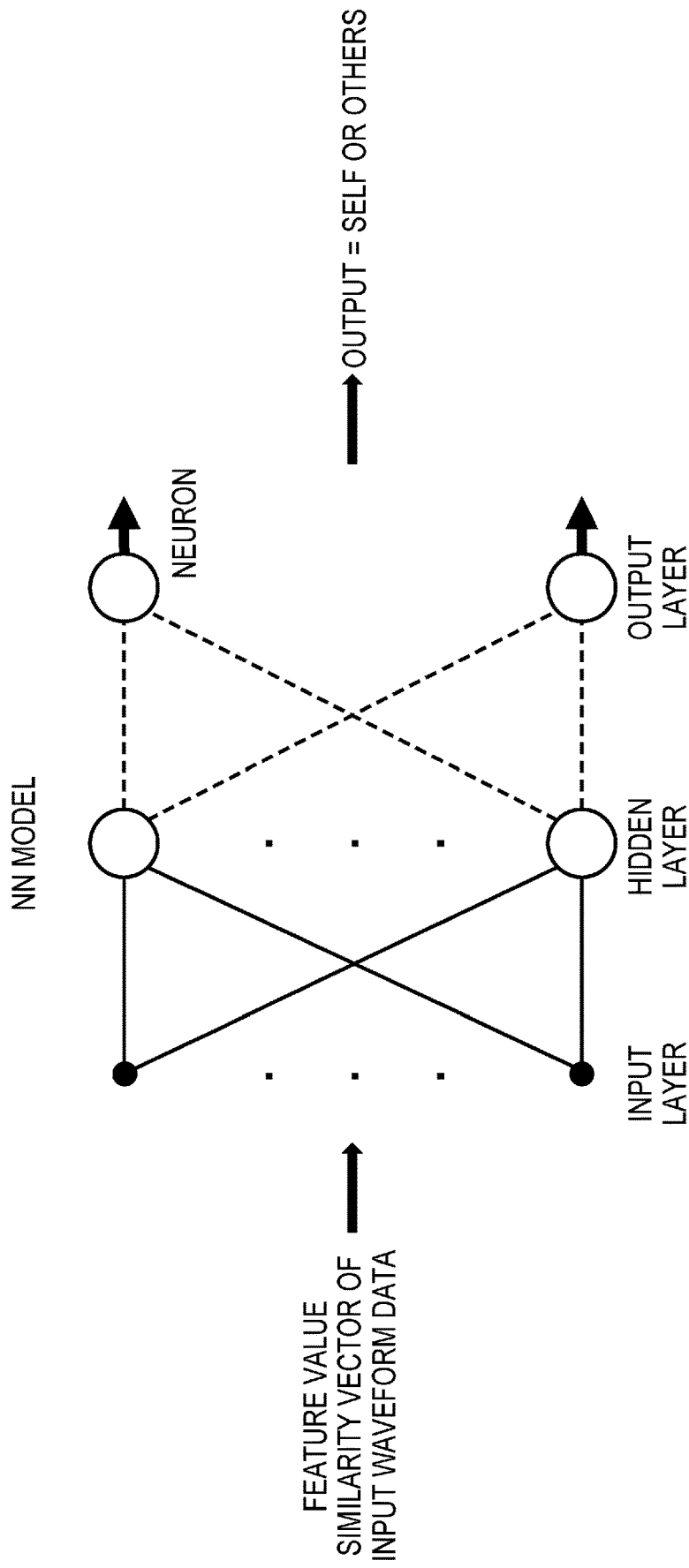
FIG. 13 is a diagram schematically illustrating an authentication process using an NN model.

FIG. 13 is a diagram schematically illustrating the authentication process using the NN model. The NN model is an average NN model or a personal NN model. In response to the input of the feature value similarity vector of the feature value set of the electrocardiogram waveform data to the NN model, the user is determined to be the "authorized user" if the resulting output value is equal to or greater than a preset threshold value, and the user is a "non-authorized user" (another person) if the output value is less than the threshold value.

In a case where there is a personal NN model such that the user is authenticated as the "authorized user" by the average NN model in the first step of authentication process and the user is authenticated as the "authorized user" also through the authentication using the personal NN model in the second step of authentication process, in other words, in a case where the user is authenticated as the "authorized user" by both NN models, the user is first determined to be the "authorized user", and then the user is authenticated as a "non-authorized user" when the user is authenticated as a "non-authorized user" by at least one of the NN models (S712). Table 1 below indicates authentication determination depending on the output results of the average NN model and the personal NN model.

TABLE 1

| | | Personal NN Model Output | |
|---|---|---|---|
| | Final Output | Authorized | Non-authorized |
| Average NN Model Output | Authorized | Authorized | Non-authorized |
| | Non-authorized | Non-authorized | Non-authorized |

It is to be noted that, when two or more different users are determined to be the same "authorized user" through authentication using both
NN models, a user having a higher output value of the average NN model is determined to be the "authorized user".

The processes of S702 to S712 are performed for all the pieces of electrocardiogram waveform data of the user to be authenticated. For example, it is determined whether the result at S712 for more than half of the pieces of electrocardiogram waveform data indicates that the same user is determined to be the "authorized user", and if so, that user is decided to be the registered user (S714).

Performing the two-step authentication process using both the average NN model and the personal NN model makes it possible to increase the authentication accuracy. The average NN model is a model for discriminating two states: authorized user (person himself/herself) and non-authorized user (another person) from pieces of electrocardiogram signal data of a certain number of users on the basis of the characteristics of probability distribution of the feature value similarities of the selves class and the others class. Such a model can be subjected to initial screening. The personal NN model determines whether each user is the authorized or non-authorized user. However, the user having been determined to be the authorized person may actually belong to the others class due to fluctuations and variations in the personal electrocardiogram signal data. Therefore, the threshold value for the output value of a conventional personal NN model has to be set relatively high, and as a result, the false rejection rate (FRR) tends to be high. The average NN model is trained using pieces of electrocardiogram signal data of a plurality of users, has a wide tolerance range for changes, and can also absorb a certain amount of difference between persons to reduce the false acceptance rate (FAR). Then, in the case of determining a user to be the authorized user by the average NN model, the threshold value of the personal NN model can be reduced to some extent, thereby increasing the accuracy of determining the user to be the authorized user and reducing the false rejection rate (FRR).

Update Phase

The update phase is a process of updating the feature values of the template waveform data registered in the database. The template waveform data (or its feature values) and the personal NN model for each user registered in the database are created from a plurality of pieces of electrocardiogram waveform data for each user obtained by measurement (the "feature value extraction process" and the "NN model creation process" in the registration phase). Updating the template waveform data with the latest electrocardiogram waveform data to cope with a change in the electrocardiogram signal pattern with time makes it possible to maintain the authentication at high accuracy. Accordingly, the electrocardiogram waveform data determined to be the "authorized user" in the authentication phase is additionally registered, and the template waveform data, the personal NN model, and the average NN model are updated using the registered electrocardiogram waveform data.

Update Process (S800)

Figure 14:
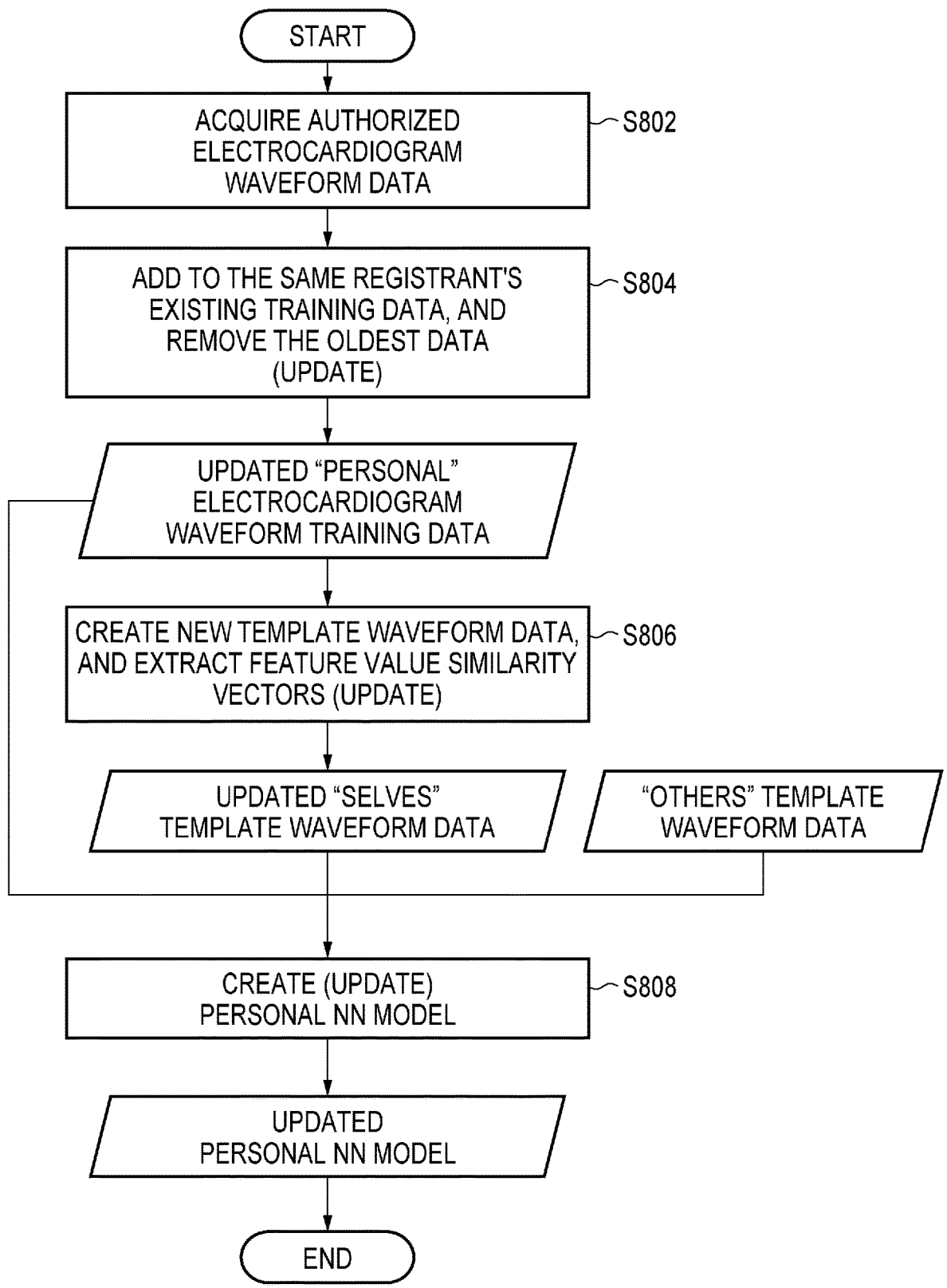
FIG. 14 is a flowchart of a personal NN model update process.

FIG. 14 is a flowchart of the personal NN model update process. In the two-step authentication process (S700) described above, the electrocardiogram waveform data of the user to be authenticated determined to be the "authorized user" is acquired (S802), and additionally registered in the database (S804). It is to be noted that if an upper limit is set for the number of registered electrocardiogram waveform data for each user and that number has already reached the upper limit, the oldest electrocardiogram waveform data is deleted, and the electrocardiogram waveform data most recently authenticated as the "authorized user" and acquired this time is registered. As such, the registered electrocardiogram waveform data is updated to newer electrocardiogram waveform data.

The old data which was obtained by extracting the feature values of the template waveform data created using the electrocardiogram waveform data and was registered in the database is updated to template waveform data and a set of feature values which are newly created and extracted (S806). Further, the personal NN model is created and trained using the updated template waveform data and the updated electrocardiogram waveform data, and thus updated (S808). It is possible to create a personal NN model coping with a change in the electrocardiographic pattern of the user with time.

FIG. 15 is a flowchart of the average NN model update process. When the electrocardiogram waveform data of a new user is added, the electrocardiogram waveform data of the new user is added to the database, and the electrocardiogram waveform data of the user to be authenticated (existing registered user) who has been determined to be the "authenticated user" in the two-step authentication process (S700) described above is acquired. The acquired electrocardiogram waveform data is additionally registered in the database (S810). As described above, also in the additional registration of electrocardiogram waveform of the existing registered user, if an upper limit is set for the number of registered electrocardiogram waveform data for each user and that number has already reached the upper limit, the oldest electrocardiogram waveform data is deleted, and the electrocardiogram waveform data most recently authenticated as the "authorized user" and acquired this time is registered. As such, the registered electrocardiogram waveform data is updated to newer electrocardiogram waveform data.

The old data which was obtained by extracting the feature values of the template waveform data of all the registered users created using the additionally registered (i.e., updated) electrocardiogram waveform data and was registered in the database is updated for all the registered users to template waveform data and sets of feature values which are newly created and extracted (S812). Then, the average NN model is created and trained using the updated template waveform data and the updated electrocardiogram waveform data, and thus updated (S814). It is possible to create an average NN model coping with addition of a new user or a change in the electrocardiographic pattern of the existing user with time.

The update process is performed periodically (e.g., every day, every week, every month) or at any time. The update at any time is performed when a predetermined condition is satisfied. It is, for example, in a maintenance process as appropriate, a case where it is determined that there is a large difference between the set of feature values as input at the time of authentication and the set of feature values of the registered template waveform data, or a case where an increased number of new users reaches a predetermined number.

The present invention can be used in various authentication situations, such as login and application authentication in smartphones and personal computers, entrance door key authentication, automobile door lock and engine start authentication, bank card and credit card authentication, identity verification in bank ATMs and various terminal devices, entrance and exit authentication (entrance and exit in safes, financial institutions, apartment buildings, etc.), user authentication at libraries, identity verification for immigration control at airports, and identity verification at medical institutions.

The present invention can also be employed for either one-to-one authentication or one-to-N (multiple) authentication.

The present invention is not limited to the above-described embodiment, and design changes within a scope without departing from the spirit of the present invention, including various variations and modifications which may be conceived by a person having ordinary skill in the art, are included in the present invention, as a matter of course.

The invention claimed is:

1. An authentication device comprising:
an electrocardiographic waveform data creation unit configured to create a plurality of pieces of electrocardiogram waveform data extracted for each heartbeat from electrocardiogram signals of a plurality of users;
a similarity calculation unit configured to calculate a similarity between each piece of electrocardiogram waveform data of each user and template waveform data created by averaging pieces of electrocardiogram waveform data of the each user;
a neural network model creation unit configured to create and train a first neural network model for every user by using similarities between pieces of electrocardiogram waveform data of a user and the template waveform data of the same user and similarities between pieces of electrocardiogram waveform data of one user and the template waveform data of another user, and create and train a plurality of second neural network models for respective users by using similarities between pieces of electrocardiogram waveform data of a certain user and the template waveform data of the certain user and similarities between pieces of electrocardiogram waveform data of the certain user and the template waveform data of another user different from the certain user; and
an authentication unit configured to, at the time of authentication, execute a first step of authentication process in which the similarities calculated using electrocardiogram waveform data for authentication created from electrocardiogram signals of a user to be authenticated and the template waveform data are input to the first neural network model created and trained in advance, and execute a second step of authentication process in which the similarities are input to the second neural network model created and trained in advance.

2. The authentication device according to claim 1, wherein the pieces of electrocardiogram waveform data and the template waveform data include a QRST wave and a QRS wave for each heartbeat.

3. The authentication device according to claim 2, further comprising the pieces of electrocardiogram waveform data and the template waveform data further include at least one of a difference wave of the QRST wave, a difference wave of the QRS wave, a kurtosis of the QRST wave, a kurtosis of the QRS wave, and a vertical height of an R peak for each heartbeat.

4. The authentication device according to claim 1, wherein the authentication unit is configured to authenticate the user as the authorized user when the first step of authentication process is successful and the second step of authentication process is successful.

5. The authentication device according to claim 1, further comprising an update unit configured to update the template waveform data of the user corresponding to the authorized user using the pieces of electrocardiogram waveform data of the authorized user as authenticated at the authentication by the authentication unit, and further update the second neural network model of the user using the updated template waveform data.

6. The authentication device according to claim 1, wherein
the electrocardiographic waveform data creation unit is configured to create a piece of electrocardiogram waveform data for authentication based on an electrocardiogram signal input at the time of authentication, and
the similarity calculation unit is configured to calculate the similarity based on the piece of electrocardiogram waveform data for authentication.

7. An authentication method comprising:
creating a plurality of pieces of electrocardiogram waveform data extracted for each heartbeat from electrocardiogram signals of a plurality of users;
calculating a similarity between each piece of electrocardiogram waveform data of each user and template waveform data created by averaging pieces of electrocardiogram waveform data of the each user;
creating and training a first neural network model for every user by using similarities between pieces of electrocardiogram waveform data of a user and the template waveform data of the same user and similarities between pieces of electrocardiogram waveform data of one user and the template waveform data of another user, and creating and training a plurality of second neural network models for respective users by using similarities between pieces of electrocardiogram waveform data of a certain user and the template waveform data of the certain user and similarities between pieces of electrocardiogram waveform data of the certain user and the template waveform data of another user different from the certain user; and
at the time of authentication, executing a first step of authentication process in which the similarities calculated using electrocardiogram waveform data for authentication created from electrocardiogram signals of a user to be authenticated and the template waveform data are input to the first neural network model created and trained in advance, and executing a second step of authentication process in which the similarities are input to the second neural network model created and trained in advance.

8. A non-transitory computer-readable storage medium storing therein a program for causing a computer to execute a process comprising:

creating a plurality of pieces of electrocardiogram waveform data extracted for each heartbeat from electrocardiogram signals of a plurality of users;

calculating a similarity between each piece of electrocardiogram waveform data of each user and template waveform data created by averaging pieces of electrocardiogram waveform data of the each user;

creating and training a first neural network model for every user by using similarities between pieces of electrocardiogram waveform data of a user and the template waveform data of the same user and similarities between pieces of electrocardiogram waveform data of one user and the template waveform data of another user, and creating and training a plurality of second neural network models for respective users by using similarities between pieces of electrocardiogram waveform data of a certain user and the template waveform data of the certain user and similarities between pieces of electrocardiogram waveform data of the certain user and the template waveform data of another user different from the certain user; and at the time of authentication, executing a first step of authentication process in which the similarities calculated using electrocardiogram waveform data for authentication created from electrocardiogram signals of a user to be authenticated and the template waveform data are input to the first neural network model created and trained in advance, and executing a second step of authentication process in which the similarities are input to the second neural network model created and trained in advance.

* * * * *